United States Patent [19]

Topham

[11] 3,957,052

[45] May 18, 1976

[54] PUMPING-SYRINGE

[75] Inventor: Silas Charles Topham, Orem, Utah

[73] Assignee: Medical Development Corporation, Salt Lake City, Utah

[22] Filed: Sept. 13, 1974

[21] Appl. No.: 505,785

[52] U.S. Cl. .................................................. 128/278
[51] Int. Cl.² ........................................... A61M 1/00
[58] Field of Search ........ 128/218 G, 218 P, 218 R, 128/218 F, 274–278

[56] References Cited
UNITED STATES PATENTS

| | | | |
|---|---|---|---|
| 297,989 | 5/1884 | Hardin | 128/278 |
| 657,440 | 9/1900 | McCaw | 128/278 |
| 714,738 | 12/1902 | Perry | 128/278 |
| 1,496,126 | 6/1924 | Livingstone | 128/218 G |
| 1,771,219 | 7/1930 | Hein | 128/218 P |
| 2,421,959 | 6/1947 | Norris | 128/278 |
| 2,705,494 | 4/1955 | Broadwin | 128/218 F |
| 3,572,375 | 3/1971 | Rosenberg | 128/274 |

Primary Examiner—William E. Kamm
Assistant Examiner—Henry S. Layton

[57] ABSTRACT

A pumping syringe and attachment for withdrawing fluids from patients and other objects, wherein the fore part of the syringe is provided with a T-passageway configuration accommodating double check valves which need not be spring loaded. Successive withdrawals of the plunge relative to the barrel of the syringe produces successive withdrawals of respective charges of withdrawn liquid; subsequent, respective depressions automatically change the fluid circuit, via check valve self-adjustment, so that fluid is ejected into a laboratory-type or other container or sump.

8 Claims, 4 Drawing Figures

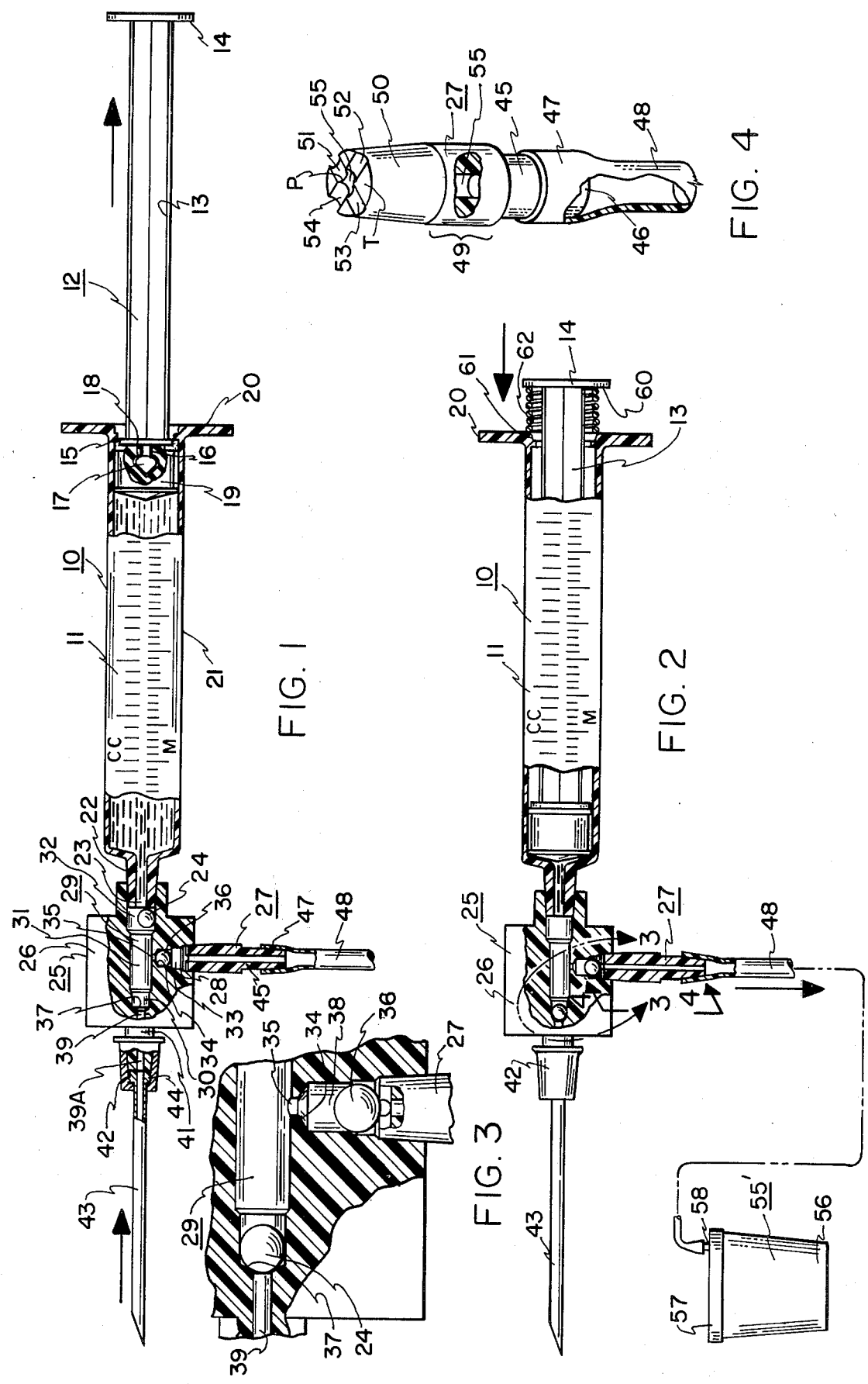

PUMPING-SYRINGE

The present invention relates to syringes and, more particularly, to a specialized syringe which is referred to hereinafter simply as a pumping syringe.

The object of such pumping syringe is to provide a means whereby fluid may be pumped from the knee of a patient, or some other part of the body or other object, in a manner that the syringe device employed need not be removed for the purpose of discharging syringe contents.

In the past, when body fluids were to be withdrawn through the patient's epidermis, a large volume syringe would be used as an evacuation device. Thus, the plunger would be withdrawn and then the cannula withdrawn from its penetration position, or simply unscrewed from the syringe, so that the barrel of the syringe can be discharged into an external container or other sump.

It would, of course, be more in accordance with the practices of sterile techniques for the cannula to remain in position in the patient as successive quantities of fluid are withdrawn and discharged from the syringe.

It must be observed here that various types of withdrawals or taps as they are termed, may involve biological liquids of widely varying viscosities and natures. Thus, the liquid of a spinal tap or hemotology investigations is much different than simply "water on the knee." Accordingly, for any valving arrangement to be successful with a syringe construction, the same must carefully avoid use of flapper valves, springs, and similar structure wherein highly viscous or sticky substances, with which the instrument would be used, will not interfere with the mechanism of the device.

Certain U.S. patents are peripherally related to the problem but none show the structural promise needed for an instrument usable in a wide area of applications. These prior approaches are given representively in the following U.S. Pat. Nos. Lee, Pat. No. 2,073,069; Calinog, 3,703,899; Hunter, 3,081,770; Hsi Hu, 2,646,042; Juhl, 1,831,668; Moe, 2,711,734.

The present invention, in contrast, takes an entirely different approach in the use of a pair of self-adjusting ball valves which need not be spring biased. These valves may be formed of stainless or surgical steel, plastic, are very small, and have proven to operate satisfactorily in a wide range of conditions.

Accordingly, in the present invention a syringe is provided, either integrally or as an attachment, with a generally T-configured flow-type block suitably valved by the ball checks as above described. The balls used, however, do not incorporate the usual biasing springs and themselves indeed are suitable, by virtue of the suction introduced into the syringe system, for performing the intended function. The central passageway in the flow block of the invention incorporates a valve seat in a direction towards the cannula and also a seat proximate a connecting orifice centrally of and beneath the block. A special type of connector is used to provide the necessary flow passage for expelling the fluid through the connector to a connecting conduit. The end result is that the plunger can be successively actuated to withdraw and then eject the fluid from a patient without requiring the cannula to be withdrawn from the patient during the operation, merely by example.

In an alternative embodiment of the invention a compression spring is used to return the plunger to an outer position automatically so that the user need only successively depress the plunger without concerning himself about how his hand position should be altered to achieve a plunger-withdrawal; also, one hand can remain free for other work.

The balls used as valves in this invention are extremely lightweight and of the order of 3/16 inch in diameter. The alternate suction strokes of the device are sufficient to draw the lower valve upwardly and to withdraw the remaining valve inwardly so that the correct flow pattern is achieved for both withdrawal and return strokes as the ball valves alter their respective positions to "open" and "close" positions.

Accordingly, a principal object of the present invention is to provide a new and improved pumping-syringe.

A further object is to provide a pumping-syringe wherein the cannula needle of the same need not be withdrawn or disconnected after each stroke.

An additional object is to provide a double ball valve construction for a syringe of a type of which highly viscous and irregular body fluids may be accommodated by the syringe for the withdrawal and ejection in a continuous manner.

An additional object of the invention is to provide a valve construction suitable for attachment to a conventional syringe so as to convert such syringe to a pumping-syringe not requiring cannula removal for continuous pumping operation thereof.

An additional object is to provide a new and improved structure for tapping and removing in a continuous manner, without loss of physical contact, body fluids of various characters and viscosities through the skin of a patient or the outer layer of another object.

An additional object is to provide an adaptor construction for existing syringes to convert the same to the pumping-syringe of the invention.

The features of the present invention may best be understood by reference to the following description taken in connection with the accompanying drawings in which:

FIG. 1 is a side elevation partially broken away and sectioned, of a pumping-syringe incorporating the features of the present invention in one embodiment thereof.

FIG. 2 is similar to FIG. 1 but shows the syringe plunger as being closed home, and with an optional return spring being utilized to return the plunger toward its outermost position.

FIG. 3 is an enlarged detail, shown principally in section, and taken along the arcuate line 3—3 in FIG. 2.

FIG. 4 is a perspective view, partially broken away and sectioned, of the connector member used in the invention to connect external conduit to the fluid flow block of the subject syringe construction.

In FIG. 1 the pumping-syringe 10 of the present invention includes a barrel 11 and a plunger 12. Plunger 12 is provided with a shank 13 equipped with a thumb-pressure plate 14 and also with a disk end 15, the latter being provided with a pin portion 16 and an enlarged head 17. The pin 16 and head 17 provide for easy insertion into the aperture 18 which is formed interior of piston 19.

Barrel 11 includes an annular finger flange 20, a straight cylinderical barrel portion 21 and also an integral forward portion 22 of reduced diameter. The latter accommodates a central liquid orifice 23 which is smaller in cross-section than the outside diameter of valve ball 24. Valve ball 24 forms a part of a valving structure 25 comprising a flow block 26 and a connector 27 threaded therein or otherwise secured thereto at 28. Primary fluid passageway 29 includes connecting, smaller, intermediate, and larger aperture portions 30–32.

The flow block 26 is provided with a communicating ejection passageway 33 which receives connector 27 and is contiguous with a valve seat 34. As to the latter, valve seat 34 forms a part of opening 35 which communicates with passageway 29. Valve ball 36 is of the order of 3/16 inch in diameter and is designed to seat into the valve seat 34. Correspondingly, a valve seat 37 is supplied, as shown in FIG. 1, and is constructed for cooperation with valve ball 24. Outlet orifice 39 continues at 39A and forms a central bore of apertured boss 41. The cup-shaped flange mount 42 incorporates cannula needle 43 which has a raised threaded boss 44 threading into the flange. Member 41 may comprise a tapered Leur fitting over which the cup-shaped flange 42 is mounted. Connector 27, see FIG. 4, has an interior passageway 55 and a hollow base portion 45 which may have a tapered exterior 46 receiving the end 47 of conduit 48. Intermediate portion 49 of the connector is enlarged relative to portion 45 and is contiguous with a tapered end portion 50 provided with recessed passageways 51–54 which are arranged in quadrature. These will be of less width at their greatest width dimension than valve ball 36, this so that the ball, when it assumes its normal position as shown in FIG. 2, will descend simply on the four points P of the cross-groove configuration at the top T of FIG. 4. Container 55' may include any type of container vessel 56 and lid 57 having at least one port 58 provided for admittance exhausted by the subject pumping-syringe.

It is to be noted that the structure 25 including flow block 26 and its related equipment, may be used as a conversion attachment for converting any conventional syringe 10 to the pumping-syringe shown.

In operation, the needle 43 is inserted into the patient or object from which fluid is to be withdrawn. The operator will watch very carefully for any entrance of blood into chamber 30 on initial plunger pull-back.

Assuming that the needle 43 is properly placed in the patient and that the desired fluid is there immediately available for withdrawal, the plunger 12 will be withdrawn so that the fluid is sucked into passageway 39 of flow block 26 and past the now inactive, unseated valve ball 24 and to the interior of the barrel 11. It is noted at this juncture that the valve ball 24, by virtue of the suction created by plunger 12, is pulled back away from its valve seat 37; simultaneously, and owing to the same suction, valve ball 36 is pulled upwardly against its seat 34 so as to close the passageway 38 to the flow of fluid downwardly or air or fluid upwardly. Thus, all of the fluid proceeds into the barrel, to the full extent of travel of plunger 12. Then, and without the necessity of withdrawing the cannula needle 43 from the patient, the medical personnel using the device simply urges the plunger forwardly, such action creating a fluid pressure which urges valve ball 24 in FIG. 1 to the left to its seat 37 as shown in FIG. 3. Subsequently, the fluid pressure will descend through the communicating opening 35 leading to opening 38. Such pressure fluid will flow past the ball, specifically of lesser outside diameter than the passageway 38 within which it is placed, and will proceed into passageways 51–54 and out the interior passageway 55 of connector 27. It is to be noted that, in similar fashion, passageway portions 31 and 32 will be of larger cross section than that of valve ball 24.

The condition of the apparatus shown in FIG. 2 illustrates that, with the return of fluid as per FIG. 3, the closing of valve ball 24 with respect to valve seat 37, and the opening of valve ball 36 relative to its seat 34, enables a discharge directly down through connector 27 and through conduit 48 to container or collector vessel 55l, and this without even requiring the separation of the cannula needle 43 from the patient. Subsequently, the plunger is returned in the direction of the arrow shown in FIG. 2 so as to accomplish, firstly, an ejection of fluid from the syringe into the container 551 and also to condition the syringe for the next pumping action, namely, the withdrawal of a second charge of fluid from the patient as by withdrawing the plunger 12 in the direction of the arrow shown in FIG. 1. Accordingly, successive withdrawals and returns of the plunger effects withdrawals of fluid from a patient and subsequent discharge into the conduit 48 leading to collector vessel or container 55'.

FIG. 2 illustrates that where desired, a compression spring 62 may be provided between undersurface 60 of plate 14 and a retainer shoulder 61 centrally provided the barrel 11 so that such spring can aid in successive withdrawals of the plunger to the effect successive withdrawals of fluid from the particular patient or specimen with which the device is used. Accordingly, in such a case the user need only depress with his thumb the plate 14 and remove from pressure only when plunger withdrawal under spring pressure via spring 62 is used.

It is important to note that after the pumping action by the subject syringe has been completed, then the syringe structure may be simply disconnected from the cannula and a new syringe, filled with a desired injection solution, be connected to subject cannula. Accordingly, the cannula needle need not be withdrawn and then subsequently reinserted for injection of desired medicament. Hence, an accumulation of water-type fluid at the knee of a patient can be conveniently withdrawn by the subject pumping-syringe as aforesaid, and cortizone, for example, injected through the same cannula.

The subject invention is suitable not only for joint areas and spinal taps, but also for thoracic work. It is to be noted that the invention is likewise suitable for the fluid substances of various types of foods, and so forth. In similar fashion, chemical solutions can be made subject to withdrawal and test.

While particular embodiments of the invention have been shown and described, it will be obvious to those skilled in the art the various changes and modifications which may be made without departing from the essential features of the present invention and, therefore, the aim in the appended claims is to cover all such changes and modifications as fall within the true spirit and scope of the invention.

I claim:

1. A pumping-syringe including, in combination: a barrel having a finger flange and a forward end provided with a liquid orifice communicating with the interior of said barrel; a plunger having a piston sealingly disposed within said barrel and a shank secured to said piston and extending outwardly of said barrel; valving structure integral with said barrel and having a cannula mount provided with a fluid opening, said valving structure defining a rectilinear, primary fluid passageway between said cannula mount at said opening and said liquid orifice, and a first ball valve seat, said valving structure including an ejection passageway intersecting said primary fluid passageway and including a reverse-ejection flow, second valve seat proximate such intersection, a first ball valve operatively disposed and retained in said primary fluid passageway and of greater transverse size than the intersection of said ejection passageway with said primary fluid passageway and also than said liquid orifice whereby said first ball valve is engageable with said forward end as a stop without passing into said liquid orifice, a second ball valve operatively disposed and retained in said ejection passageway and positioned to seal selectively against said second valve seat upon vacuum, withdrawal strokes of said plunger, and a cannula mounted to said cannula mount.

2. The device of claim 1 wherein said pumping-syringe is also provided with compression spring means operatively disposed with respect to and reacting against said barrel and plunger for spring-biasing said plunger rearwardly with respect to said barrel.

3. The device of claim 1 wherein said plunger includes a thumb plate, said spring surrounding said plunger and abutting in respective directions toward said thumb plate and also said barrel proximate said finger flange thereof.

4. The device of claim 1 wherein said barrel has a boss provided with a hollow interior defining said liquid orifice, said valving structure having a mounting port communicating with said primary fluid passageway and mountingly interiorly receiving said boss.

5. The device of claim 1 wherein said valving structure comprises a separate component communicatively mounted to said barrel such that said primary fluid passageway operatively communicates with the interior of said barrel.

6. The device of claim 1 wherein said pumping-syringe includes an axially hollow connector member constructed for receiving exhaust conduit and having an undulatingly configured, valve-supporting end means, secured to said valving structure proximate said ejection passageway, for permitting flow past said second ball valve across said undulatingly configured end means and axially through said connector member.

7. As an attachment for a syringe, having a cannula and a syringe barrel, for convering said syringe to a pumping-syringe: a valving block having inlet, outlet, and ejection ports, said inlet port being constructed for connection to said cannula, said outlet port being constructed for connection to said syringe barrel, said ejection port being constructed for connection to an exhaust system; first valving means disposed between said inlet and outlet ports for admitting fluid flow from said inlet port to said outlet port and for preventing reverse-flow back through said inlet port; and second valving means interposed between said outlet port and said ejection port for passing fluid from said outlet port to said ejection port and for preventing both reverse-flow thereof and also flow from said inlet port directly to said exhaust port, said first and second valving means comprising respective first and second ball valves and respective valve seats disposed in said inlet port and also in said exhaust port, respectively, said syringe barrel having an apertured end fitted into said block at said outlet port and comprising a stop abutment for said first ball valve.

8. An adaptor for a syringe, for insertion between the cannula and barrel thereof, to convert the same to a pumping-type syringe, said adaptor comprising a unitary one-piece valving block having a cannula mount, a barrel mount, and provided with ejection means, said block containing valved passageway means for conducting fluid one way, from said cannula mount to said barrel mount upon syringe-plunger withdrawal, and for conducting fluid from said barrel solely to said ejection means upon plunger returns, and wherein said ejection means comprises a valve-retaining fluid conduit connector having a central bore and scalloped, interiorly disposed edge portions surrounding said control bore.

* * * * *